United States Patent
Jones (10) Patent No.: US 10,639,091 B2
(45) Date of Patent: May 5, 2020

(54) MANUFACTURING ELECTROSURGICAL INSTRUMENTS

(71) Applicant: GYRUS MEDICAL LIMITED, St Mellons, Cardiff (GB)

(72) Inventor: Lewis Meurig Jones, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1066 days.

(21) Appl. No.: 14/992,137

(22) Filed: Jan. 11, 2016

(65) Prior Publication Data
US 2016/0199122 A1     Jul. 14, 2016

(30) Foreign Application Priority Data
Jan. 14, 2015 (GB) .................................. 1500532.5

(51) Int. Cl.
*A61B 18/14* (2006.01)
*B29L 31/00* (2006.01)
(Continued)

(52) U.S. Cl.
CPC ...... *A61B 18/1442* (2013.01); *A61B 18/1445* (2013.01); *A61B 18/1402* (2013.01);
(Continued)

(58) Field of Classification Search
CPC ............ A61B 18/1445; A61B 18/1442; A61B 18/1402; A61B 2018/0063;
(Continued)

(56) References Cited

U.S. PATENT DOCUMENTS 7,150,097 B2 * 12/2006 Sremcich ........... A61B 18/1445
29/854
7,473,253 B2    1/2009 Dycus et al.
(Continued)

FOREIGN PATENT DOCUMENTS

AU     2006222705    10/2006
CN    101683282 A    3/2010
(Continued)

OTHER PUBLICATIONS

Combined Search and Examination Report Under Sections 17 & 18(3) in UK Application No. GB 1522606.1, dated May 26, 2016.
(Continued)

*Primary Examiner* — Peter Dungba Vo
*Assistant Examiner* — Kaying Kue
(74) *Attorney, Agent, or Firm* — Oliff PLC (57) ABSTRACT

A jaw member for an electrosurgical instrument is manufactured by providing a jaw housing (18) having a longitudinal jaw section (19), and an electrically conductive plate (1). The electrically conductive plate is placed into a mould, and a first flowable insulating material (15) is injected into the mould such that the flowable material (15) forms one or more stop members (16) that project a predetermined distance from the electrically conductive plate. The jaw housing (18) and the electrically conductive plate (1) are then placed into a second mould, and a second flowable material (25) is injected into the mould to secure the electrically conductive plate (1) to the jaw housing (18).

17 Claims, 9 Drawing Sheets

(51) Int. Cl.
   *B29C 45/14* (2006.01)
   *A61B 17/29* (2006.01)
   *B29C 45/12* (2006.01)
   *A61B 18/00* (2006.01)
   *A61B 17/00* (2006.01)

(52) U.S. Cl.
   CPC .............. *A61B 2017/00526* (2013.01); *A61B 2017/2936* (2013.01); *A61B 2018/0063* (2013.01); *A61B 2018/00077* (2013.01); *A61B 2018/00083* (2013.01); *A61B 2018/00607* (2013.01); *A61B 2018/1455* (2013.01); *B29C 45/12* (2013.01); *B29C 45/14639* (2013.01); *B29L 2031/7546* (2013.01)

(58) Field of Classification Search
   CPC ... A61B 2018/1405–1435; A61B 2018/00178; A61B 2017/00526; A61B 2017/2948; A61B 2018/00077; A61B 2018/00083; Y10T 29/4917; Y10T 29/4922; B29L 2031/7546; B29C 45/12; B29C 45/14639
   USPC ......... 29/876, 883, 874; 264/272.11, 272.13; 606/32–49
   See application file for complete search history.

(56) References Cited

U.S. PATENT DOCUMENTS

| | | | |
|---|---|---|---|
| 7,877,852 B2 | 2/2011 | Unger et al. | |
| 7,922,953 B2* | 4/2011 | Guerra | A61B 18/1445 264/259 |
| 8,241,284 B2* | 8/2012 | Dycus | A61B 90/03 606/51 |
| 8,246,618 B2* | 8/2012 | Bucciaglia | A61B 17/2909 606/46 |
| 8,298,232 B2* | 10/2012 | Unger | A61B 18/1445 606/51 |
| 8,439,911 B2* | 5/2013 | Mueller | A61B 17/295 606/51 |
| 8,480,671 B2* | 7/2013 | Mueller | A61B 18/1445 606/51 |
| 8,591,510 B2* | 11/2013 | Allen, IV | A61B 17/2816 606/45 |
| 9,113,941 B2* | 8/2015 | Kappus | A61B 18/1445 |
| 9,204,879 B2* | 12/2015 | Shelton, IV | A61B 34/37 |
| 10,098,689 B2* | 10/2018 | Soni | A61B 18/1442 |
| 10,130,414 B2* | 11/2018 | Weiler | A61B 18/1445 |
| 10,251,696 B2* | 4/2019 | Dycus | A61B 90/03 |
| 2003/0014053 A1 | 1/2003 | Nguyen et al. | |
| 2004/0122423 A1* | 6/2004 | Dycus | A61B 90/03 606/51 |
| 2005/0113826 A1* | 5/2005 | Johnson | A61B 18/1442 606/45 |
| 2005/0149017 A1* | 7/2005 | Dycus | A61B 18/1445 606/51 |
| 2007/0074807 A1* | 4/2007 | Guerra | A61B 18/1445 156/242 |
| 2007/0173814 A1* | 7/2007 | Hixson | A61B 18/1445 606/51 |
| 2007/0179499 A1* | 8/2007 | Garrison | A61B 18/1445 606/51 |
| 2007/0265616 A1 | 11/2007 | Couture et al. | |
| 2008/0015575 A1 | 1/2008 | Odom et al. | |
| 2009/0254081 A1* | 10/2009 | Allison | A61B 18/1445 606/39 |
| 2010/0179540 A1* | 7/2010 | Marczyk | A61B 18/1445 606/41 |
| 2012/0083783 A1* | 4/2012 | Davison | A61B 18/1445 606/45 |
| 2012/0265241 A1 | 10/2012 | Hart et al. | |
| 2013/0085496 A1 | 4/2013 | Unger et al. | |
| 2013/0185922 A1* | 7/2013 | Twomey | A61B 18/1445 29/527.1 |
| 2013/0226177 A1 | 8/2013 | Brandt et al. | |
| 2013/0253499 A1* | 9/2013 | Kimball | A61B 18/1206 606/33 |
| 2013/0255063 A1 | 10/2013 | Hart et al. | |
| 2014/0025073 A1* | 1/2014 | Twomey | A61B 18/1442 606/51 |
| 2014/0171940 A1* | 6/2014 | Reschke | A61B 18/1442 606/39 |
| 2014/0194875 A1 | 7/2014 | Reschke et al. | |
| 2015/0018816 A1 | 1/2015 | Latimer | |

FOREIGN PATENT DOCUMENTS

| | | |
|---|---|---|
| CN | 103211647 B | 12/2016 |
| EP | 1486177 | 12/2004 |
| EP | 1795140 | 6/2007 |
| EP | 2425791 | 3/2012 |
| EP | 2687176 | 1/2014 |
| WO | 9713463 A1 | 4/1997 |
| WO | 2015/197395 A1 | 12/2015 |

OTHER PUBLICATIONS

U.S. Appl. No. 14/992,193, filed Jan. 11, 2016, Thomas, et al.
U.S. Appl. No. 14/993,408, filed Jan. 12, 2016, Thomas, et al.
U.S. Appl. No. 14/993,496, filed Jan. 12, 2016, Thomas, et al.
U.S. Appl. No. 14/994,464, filed Jan. 13, 2016, Jones.
Oct. 9, 2018 Office Action issued in Chinese Patent Application No. 201610022584.1.
Search Report in UK Application No. GB 1500532.5, dated Jun. 5, 2015.

* cited by examiner

MANUFACTURING ELECTROSURGICAL INSTRUMENTS

CROSS-REFERENCE TO RELATED APPLICATION

This application claims priority to United Kingdom Application No. 1500532.5, filed 14 Jan. 2015, the entire contents of which are incorporated herein by reference.

TECHNICAL FIELD

Embodiments of this invention relate to a method for manufacturing a jaw member for an electrosurgical instrument, particularly a forceps instrument for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to manufacture jaw members for electrosurgical instruments by an overmoulding process, in which components are assembled into a mould and flowable material is introduced into the mould to surround the components and form the completed jaw member. U.S. Pat. Nos. 7,150,097 & 7,922,953 are examples of such manufacturing methods. It is also known to provide stop members on the jaw member, and U.S. Pat. No. 7,877,852 is one example of such a manufacturing method.

SUMMARY OF THE INVENTION

Embodiments of the present invention attempt to provide one or more improved alternatives to manufacturing methods such as those described in the prior art referenced above.

Accordingly, one aspect provides a method for manufacturing a jaw member for an electrosurgical instrument, comprising the steps:

providing a jaw housing having a longitudinal jaw section;

providing an electrically conductive plate;

placing the electrically conductive plate into a first mould;

injecting a first flowable insulating material into the mould, such that the flowable material forms one or more stop members that project a predetermined distance from the electrically conductive plate;

allowing the first flowable insulating material to solidify;

placing the jaw housing and the electrically conductive plate into a second mould;

injecting a second flowable insulating material into the mould to secure the electrically conductive plate to the jaw housing;

allowing the second flowable insulating material to solidify; and removing the jaw housing, electrically conductive plate and the solidified insulating material from the mould as a jaw member.

In U.S. Pat. No. 7,877,852 referred to above, the stop members are preformed in a separate insulating housing which is then assembled together with a conductive sealing plate having apertures therein, the stop members of the insulating housing protruding through the apertures. In an alternative arrangement, the stop members are dispersed in molten form into cavities formed in the sealing plate, and solidify to form the stop members. Embodiments of the present invention provide an improved alternative to either of these arrangements, in which the one or more stop members are formed during a first overmoulding process. In this way, the one or more stop members are part of the overmoulded component as opposed to a preformed component such as a housing which needs to be carefully assembled together with the other components.

Preferably, the injecting step is such that the predetermined distance is about 20 µm to about 350 µm (0.00079 inches to about 0.014 inches). By ensuring that the one or more stop members project from the electrically conductive plate by this sort of distance, effective sealing of tissue grasped between the jaw members is achieved.

The method conveniently includes the step of providing a pre-moulded insert that can be received within the jaw housing. The method conveniently comprises placing the electrically conductive plate against the pre-moulded insert before placing the electrically conductive plate into a first mould. According to one arrangement, the method includes the steps of placing the electrically conductive plate against the pre-moulded insert to form a first sub-assembly, and then placing the first sub-assembly into the first mould and injecting the first flowable insulating material. In this way, the conductive plate and the insert are pre-assembled prior to the moulding of the first flowable material. Moreover, the provision of the first flowable material acts to simultaneously form the stop members and fasten the electrically conductive plate and the pre-moulded insert together, thus forming a unified assembly that can be dealt with as a single part for the remainder of the construction method. Once the first flowable material has solidified, the unified assembly formed by the conductive plate, the insert and the now solidified first flowable material is located on the jaw housing and placed in the second mould for the application of the second flowable material.

Alternatively, the method includes the step of placing the electrically conductive plate against the pre-moulded insert after injecting the first flowable insulating material on to the electrically conductive plate and allowing it to solidify. In this arrangement, the method includes the steps of placing the electrically conductive plate against the pre-moulded insert to form a first sub-assembly, placing the first sub-assembly into the jaw housing to form a second sub-assembly, and then placing the second sub-assembly into the second mould and injecting the second flowable insulating material. This alternative method forms the one or more stop members on the conductive plate before it is located on the insert, such that the conductive plate, insert and jaw housing are only secured on to one another during the application of the second flowable material.

According to a further alternative method, the method includes the steps of placing the pre-moulded insert (after injecting the first flowable insulating material) into the jaw housing to form a first sub-assembly, placing the electrically conductive plate on to the first sub-assembly to form a second sub-assembly, then placing the second sub-assembly into the second mould and injecting the second flowable insulating material. This differs from the above method only by the order in which the components are assembled, with the insert being loaded into the jaw housing before the addition of the conductive plate.

Whichever method is employed, it conveniently includes the additional step of disposing an electrically conductive lead against the conductive plate before placing the jaw housing and the electrically conductive plate into the second mould. Conveniently, the electrically conductive wire is crimped in position before placing the jaw housing and the electrically conductive plate into the second mould. Typically, the second flowable insulating material assists in securing the lead in position in electrical connection with the conductive plate.

The electrically conductive plate is preferably provided with one or more retention features, and the first flowable insulating material flows into the one or more retention features to form the one or more stop members. According to one convenient arrangement, the one or more retention features comprise one or more recesses. Conceivably, the one or more recesses comprise a plurality of blind holes formed in the electrically conductive plate, or alternatively a trough formed in the electrically conductive plate. Alternatively, the one or more retention features comprise a plurality of passages formed in the electrically conductive plate, such as a plurality of through holes in the electrically conductive plate. The through holes allow the first flowable material to flow up through the holes in order to form the one or more stop members on the electrically conductive plate. Conveniently, the through holes are disposed along the longitudinal axis of the conductive plate.

In a preferred combination, the electrically conductive plate is provided with an elongate groove in which the plurality of through holes are located. This combines the structure of a trough together with through holes to form elongate stop members anchored by means of the first flowable material having flowed through the holes from underneath the conductive plate. Preferably the elongate groove is substantially U-shaped, so as to form one elongate stop member on each half of the electrically conductive plate. Typically, the electrically conductive plate includes a longitudinally extending slot capable of receiving a translatable knife blade, in which case the U-shaped groove produces one elongate stop member on each side of the longitudinally-extending slot.

Whichever type of retention features are provided, they are conveniently disposed adjacent the longitudinally extending slot. Typically, the one or more retention features are disposed either side of the longitudinally extending slot. Conceivably, the one or more retention features comprise one or more indents in the longitudinally extending slot.

Embodiments of the invention further reside in a method for manufacturing an end effector assembly for sealing tissue, comprising the steps of:

providing a pair of first and second jaw housings each having a longitudinal jaw section, and a pair of electrically conductive plates, at least one of the electrically conductive plates including one or more retention features therein;

placing the electrically conductive plates into first moulds;

injecting a first flowable insulating material into the moulds, such that the flowable material flows into the one or more retention features to form one or more stop members that project a predetermined distance from the electrically conductive plate;

allowing the first flowable insulating material to solidify;

placing the jaw housings and the electrically conductive plates into second moulds;

injecting a second flowable insulating material into the moulds to secure the electrically conductive plates to the jaw housings;

allowing the second flowable insulating material to solidify;

removing the jaw housings, electrically conductive plates and the solidified insulating material from the moulds to form two jaw members; and assembling the jaw members about a pivot such that the electrically conductive plates are substantially opposed to each other in pivotal relation relative to one another.

Embodiments of the invention also reside in a jaw member or an end effector for an electrosurgical instrument made in accordance with the methods as previously described.

DESCRIPTION OF THE DRAWINGS

Embodiments of the invention will now be further described, by way of example only, with reference to the accompanying drawings, in which.

DESCRIPTION OF THE EMBODIMENTS

Figure 1:
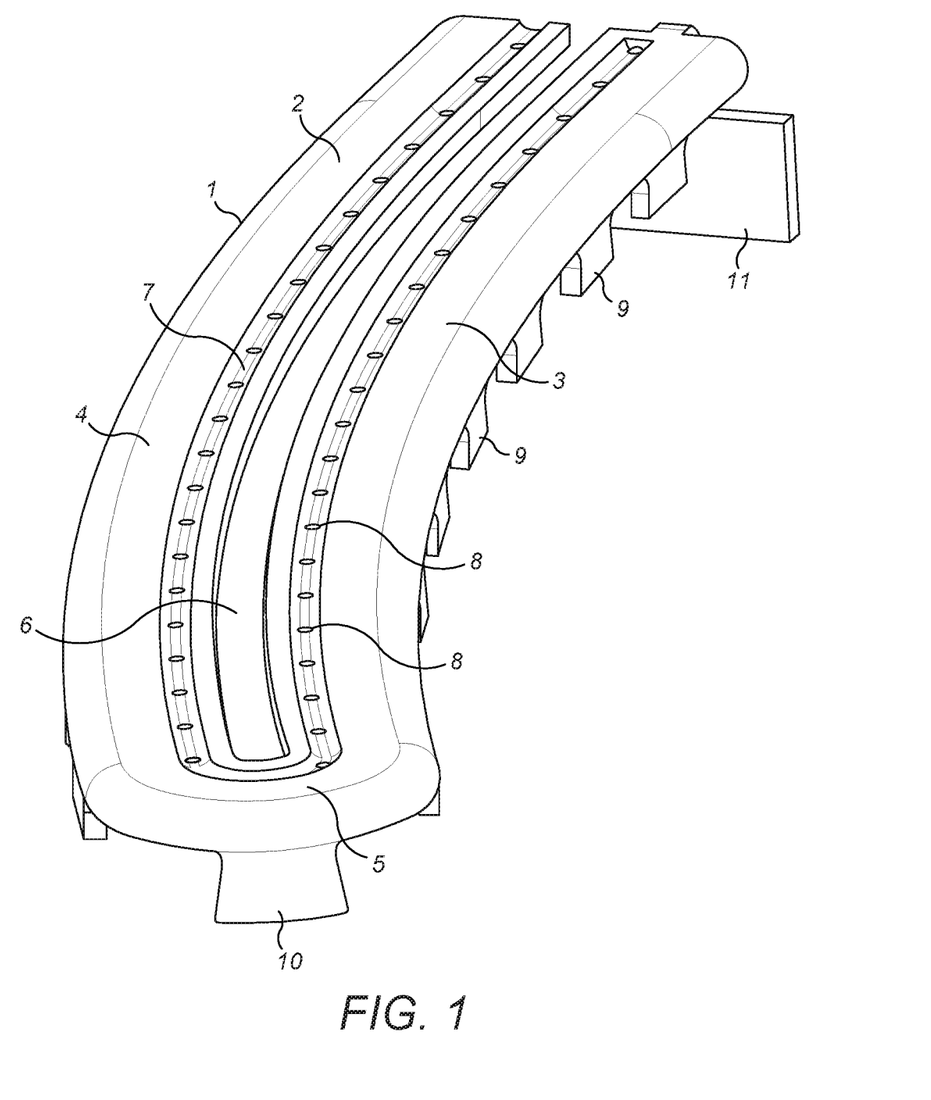
FIG. 1 is a schematic perspective view of an electrically conductive plate used in a manufacturing method in accordance with an embodiment of the present invention.
Figure 2:
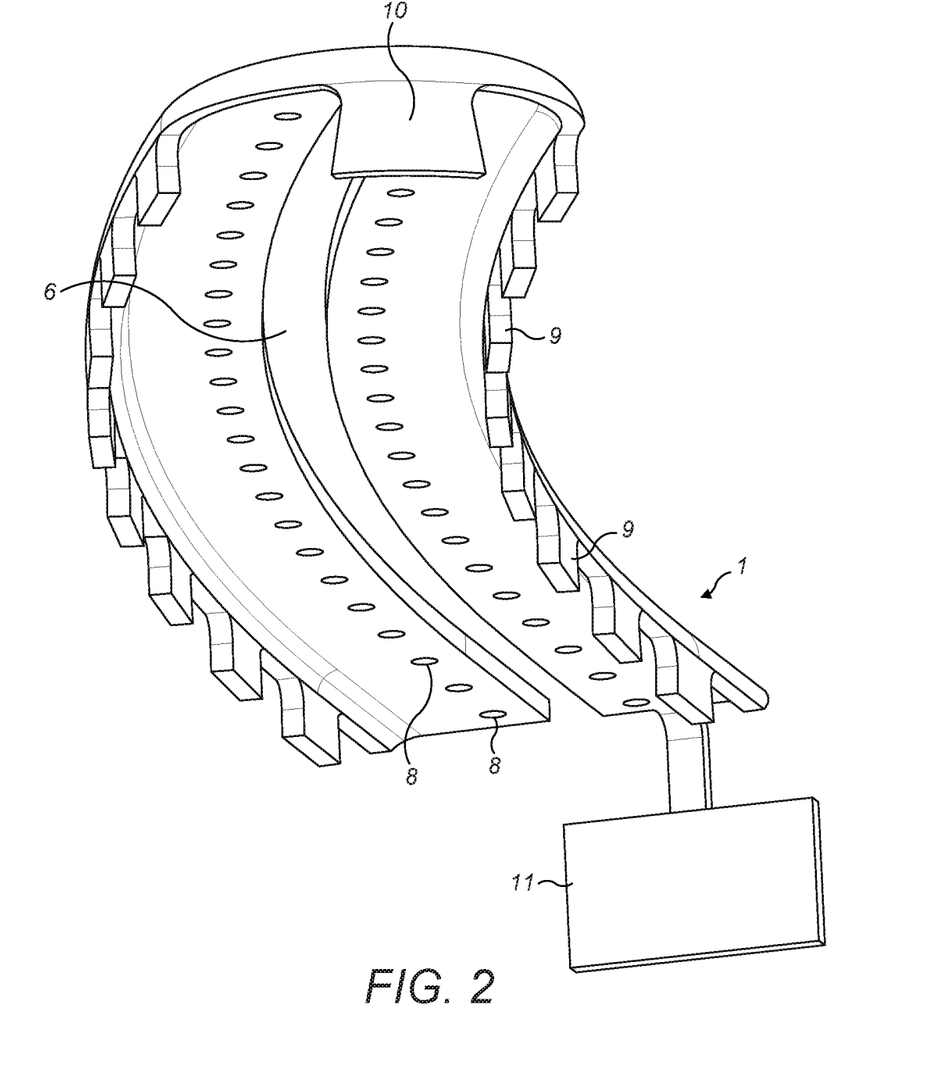
FIG. 2 is an underneath view of the electrically conductive plate of FIG. 1.

Referring to FIGS. 1 & 2, an electrically conductive plate in the form of a shim 1 is manufactured from one or more of the processes of stamping, machining etching, folding or by a casting process, and comprises an upper surface 2 including a left sealing surface 3, a right sealing surface 4, and an end portion 5. The shim has a central slot 6, and a generally U-shaped trough 7 bordering the slot 6. A plurality of through holes 8 are located in the trough 7.

Figure 3:
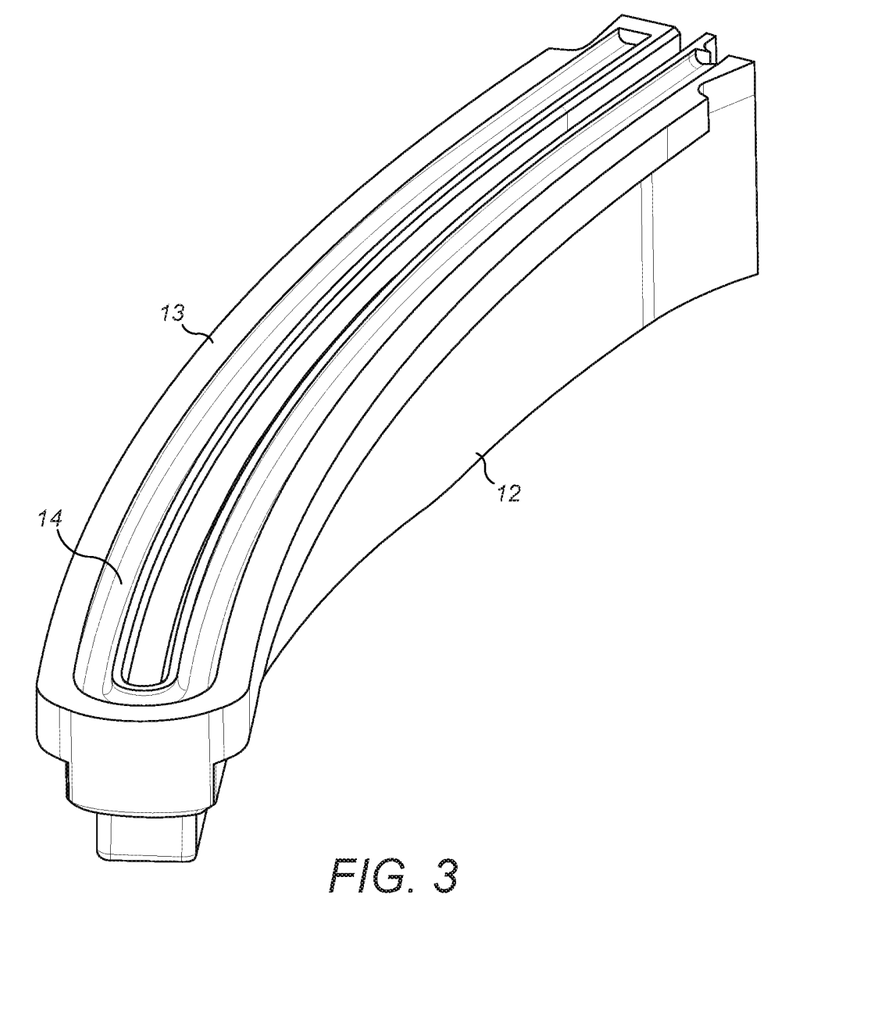
FIG. 3 is a perspective view of an insert component used in the manufacturing method in accordance with an embodiment of the present invention.
Figure 4:
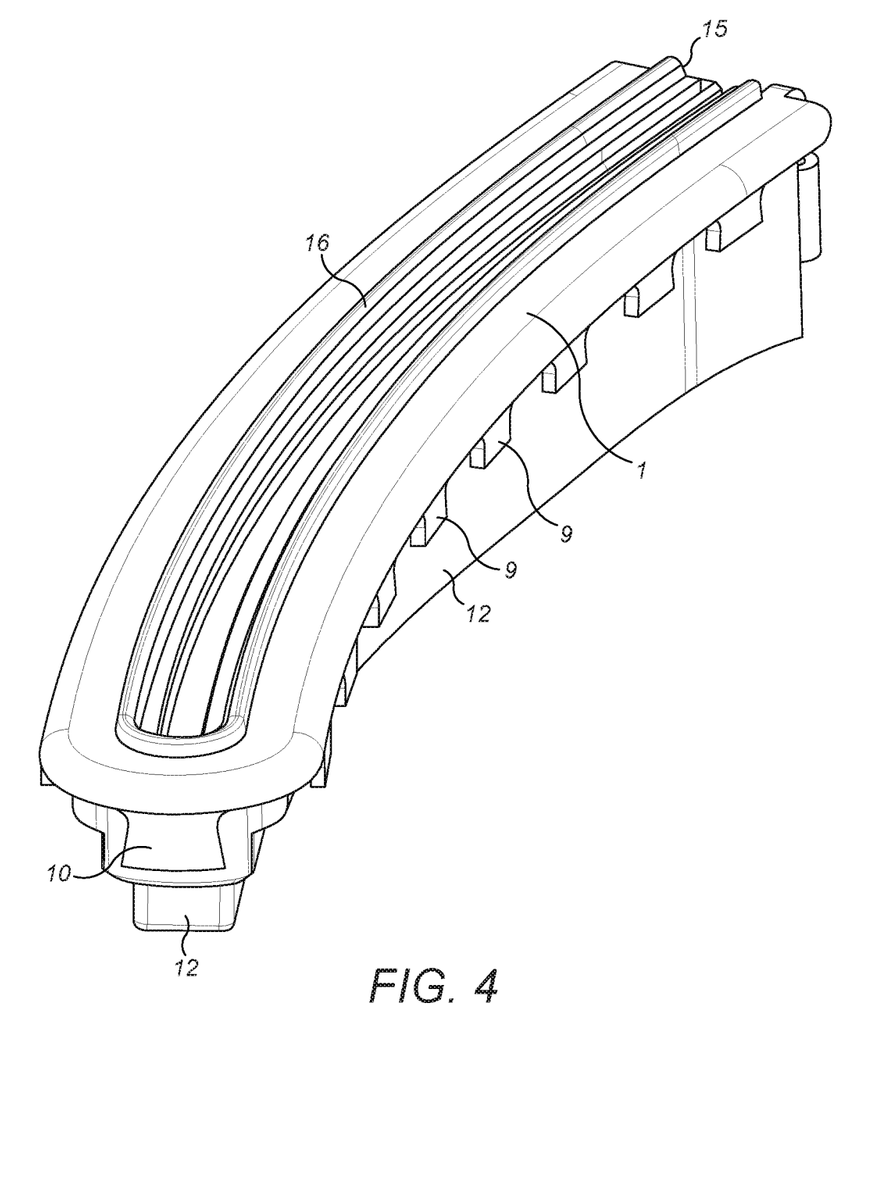
FIG. 4 is a perspective view of a the electrically conductive plate and insert component of FIGS. 1 to 3 forming a sub-component during a first manufacturing stage of the manufacturing method in accordance with an embodiment of the present invention.
Figure 5:
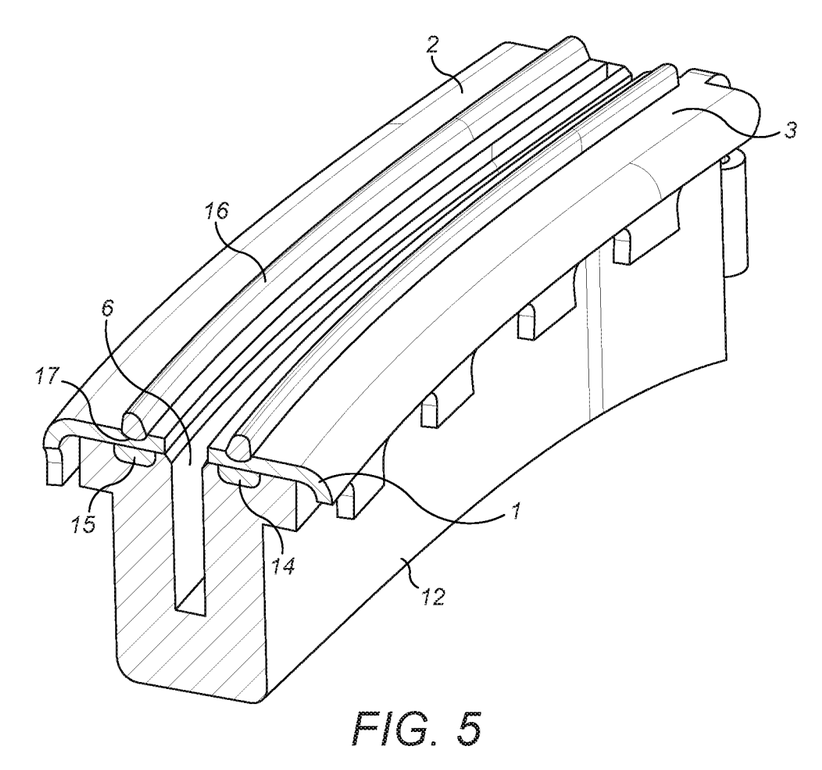
FIG. 5 is an enlarged sectional view of a portion of the sub-component of FIG. 4.

A plurality of retaining tabs 9 are present at the edges of the shim 1, the retaining tabs being equally spaced along the sides of the shim A single end tab 10 is present at the distal end of the shim, and a larger connecting tab 11 is present at the proximal end of the shim FIG. 3 shows a pre-formed polymer insert 12, having an elongate shape to generally match that of the shim 1 The insert 12 has an upper face 13 with a U-shaped groove 14 therein, the upper face of the insert being dimensioned such that the shim 1 can be received thereon. In a first manufacturing step, the shim 1 is placed on top of the insert 12, with the tabs 9 & 10 extending around the sides and front of the insert respectively. The assembled shim and insert are placed into a mould (not shown), and a flowable plastics material 15 such as silicone is injected into the mould. The plastics material 15 flows between the shim 1 and the insert 12 so as to fill any available areas, including the groove 14. The material 15 also flows through the through holes 8 and into the trough 7, forming a generally U-shaped stop member, as shown at 16 in FIGS. 4 & 5.

Figure 6:
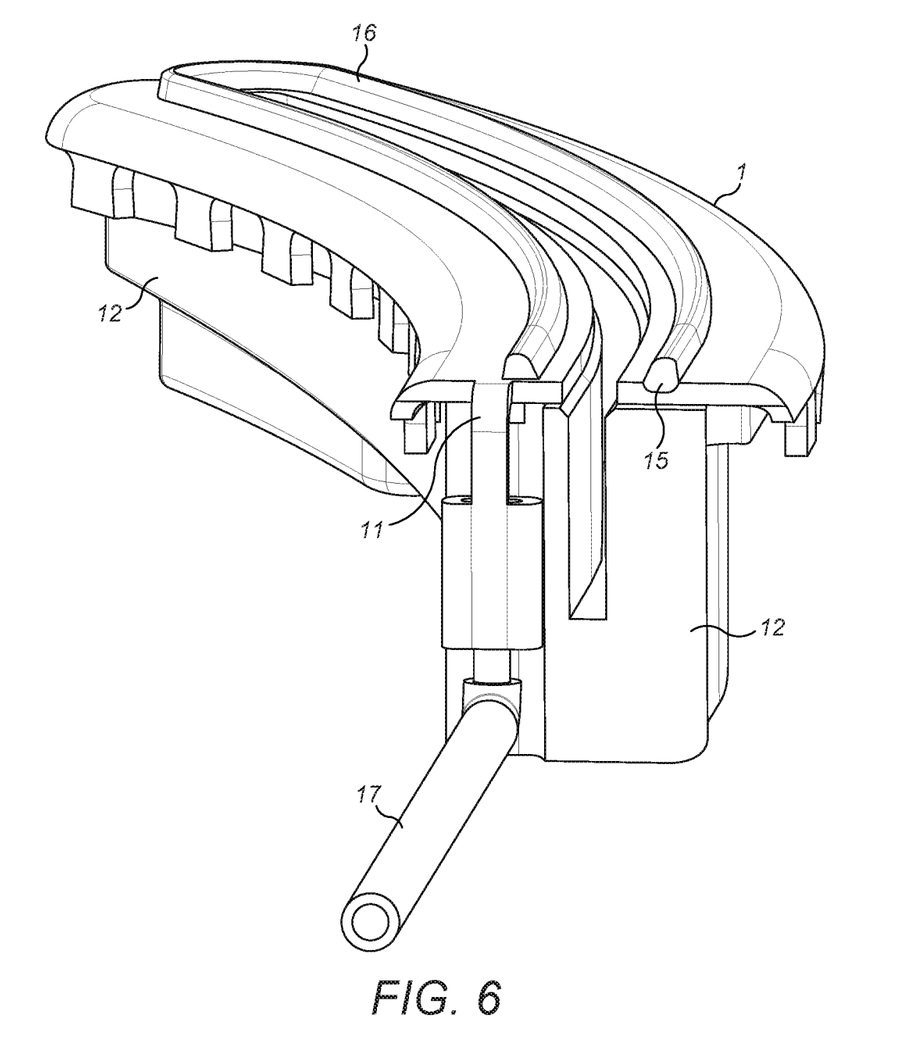
FIG. 6 is a schematic diagram of the sub-component of FIG. 4 during a further stage of the manufacturing method in accordance with an embodiment of the present invention.

The stop member 16 protrudes above the upper surface 2 of the shim by a distance of 20 µm to about 350 µm. The flowable material 15 is allowed to solidify, securing the shim 1 and insert 12 one to the other. Once secure, an electric lead 17 is attached to the connecting tab 11 at the proximal end of the shim, as shown in FIG. 6. The lead 17 is secured by soldering, crimping, or both.

In an alternative embodiment to the above, instead of the shim 1 and the insert 12 being placed in the mould together, and the flowable plastics material 15 being used to secure the shim 1 and the insert 12 together, in the alternative embodiment the shim 1 is inserted into a suitable mould without the insert 12. In this embodiment the flowable plastics material 15 is injected into the mould so as to flow through the through holes 8 and into the trough 7, forming the generally U-shaped stop member, as shown at 16 in FIGS. 4 & 5 in the same manner as before, but without also securing the shim and the insert together. In this way, the shim 1 is provided with a formed stop member 16 before it is then introduced to the plastic insert for the remainder of the process.

Figure 7:
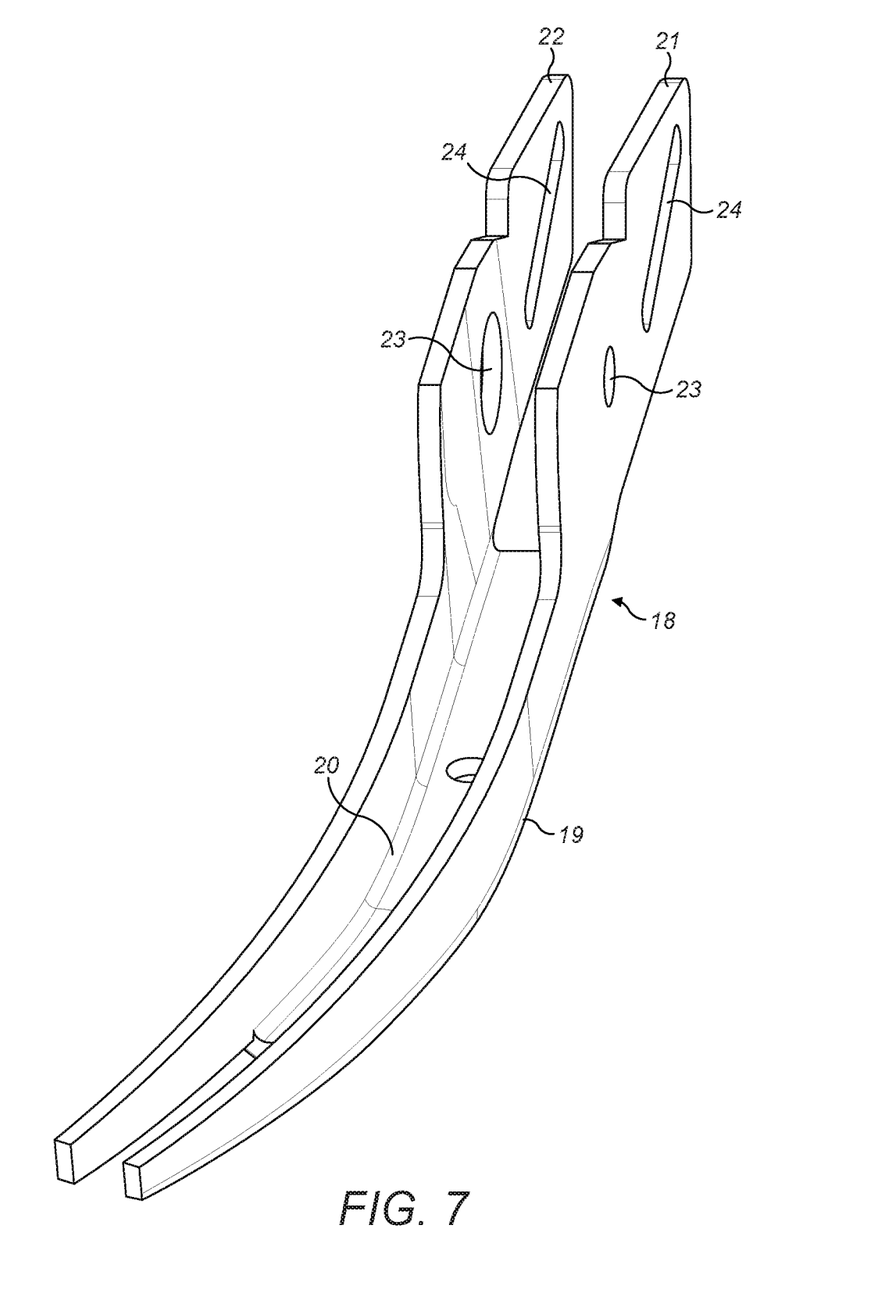
FIG. 7 is a perspective view of a jaw housing used in a final stage of the manufacturing method in accordance with an embodiment of the present invention.

FIG. 7 shows a metallic jaw housing 18 used in the next stage of the manufacturing process. The jaw housing is also manufactured either from stamping, machining, metal injection moulding or by a casting process, and comprises an elongate jaw body 19 with a generally U-shaped cross section defining a cavity 20 therein. Proximal of the jaw body 19 is a pair of flanges 21 & 22, each having a pivot aperture 23 and an angled cam slot 24.

The manufacturing process has several options at this point. In a first option, the jaw housing 18 is placed in a second mould (not shown), and the sub-assembly shown in FIG. 6 (consisting of shim 1, insert 12 and formed stop member 16) is placed in the mould on top of the jaw housing, with the lower portion of the insert being received within the cavity 20. In a second option, the sub-assembly shown in FIG. 6 is placed in the jaw housing 18 before the jaw housing is placed into the second mould. Whichever way it is done, a second flowable material 25 such as polyethylene or polypropylene is then injected into the mould and allowed to flow around the jaw housing 18 and between the jaw housing and the insert 12.

Figure 8:
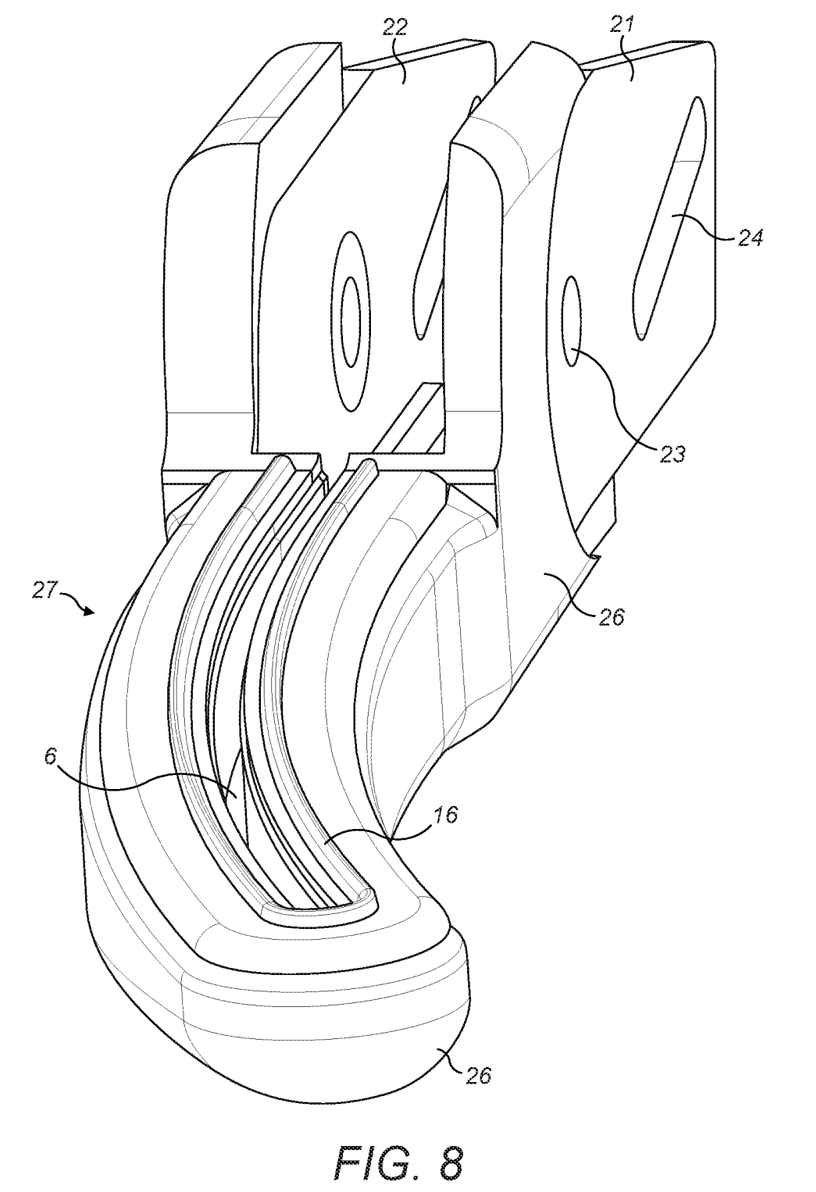
FIG. 8 is a schematic perspective view of a jaw member formed in the final stage of the manufacturing method in accordance with an embodiment of the present invention.
Figure 9:
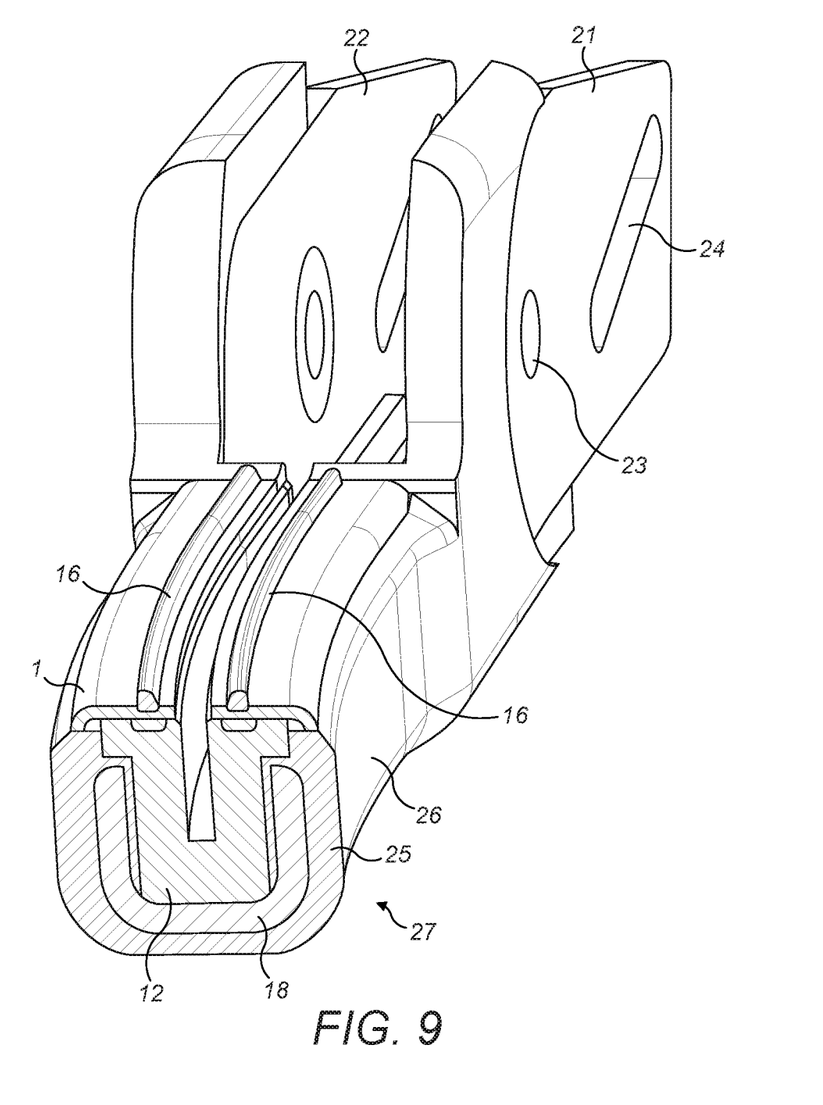
FIG. 9 is an enlarged sectional view of a portion of the jaw member of FIG. 8.

The second flowable material 25 flows between the jaw housing 18 and the sides of the mould to create a jaw body, shown at 26 in FIGS. 8 & 9. The second flowable material 25 is allowed to solidify, such that the jaw body 26 secures the shim, insert 12 and jaw housing 18 together into a completed jaw member 27, and constitutes the outer sides and bottom thereof.

The jaw member 27 can be assembled together with another similar jaw member to form an end effector for a forceps instrument, as will be known in the art for the sealing and/or cutting of tissue. The jaw member 27 can be mounted on a pivot pin (not shown) passing through the pivot apertures 23, and a cam pin (also not shown) can be located in the cam slots 24 in order to cause the pivoting of one jaw with respect to the other between open and closed positions.

Those skilled in the art will appreciate that modifications to the above can be made without departing from the scope of the present invention, and that alternative configurations of components can be employed. By providing cut-outs or through holes for the flowable material to rise up above the shim 11, stop members can be formed during a first over-moulding process, and a second overmoulding process used to secure and create the remainder of the jaw member.

The invention claimed is:

1. A method for manufacturing a jaw member for an electrosurgical instrument, the method comprising the steps of:
providing a jaw housing having a longitudinal jaw section;
providing an electrically conductive plate with one or more retention features comprising a plurality of through holes formed in the electrically conductive plate, the plurality of through holes being located in an elongate groove of the electrically conductive plate;
placing the electrically conductive plate into a first mould;
injecting a first flowable insulating material into the first mould, such that the first flowable insulating material flows into the one or more retention features to form one or more stop members that project a predetermined distance from the electrically conductive plate;
allowing the first flowable insulating material to solidify;
placing the jaw housing and the electrically conductive plate into a second mould;
subsequently injecting a second flowable insulating material into the second mould to secure the electrically conductive plate to the jaw housing;
allowing the second flowable insulating material to solidify; and
removing the jaw housing, the electrically conductive plate, the solidified first insulating material and the solidified second insulating material from the first mould and the second mould as a jaw member.

2. A method according to claim 1, wherein the injecting step is such that the predetermined distance is about 20 µm to about 350 µm (0.00079 inches to about 0.014 inches).

3. A method according to claim 1, including the step of providing a pre-moulded insert that can be received within the jaw housing.

4. A method according to claim 3, including the step of placing the electrically conductive plate against the pre-moulded insert before placing the electrically conductive plate into the first mould.

5. A method according to claim 4, including the steps of placing the electrically conductive plate against the pre-moulded insert to form a first sub-assembly, and then placing the first sub-assembly into the first mould and injecting the first flowable insulating material.

6. A method according to claim 3, including the step of placing the electrically conductive plate against the pre-moulded insert after injecting the first flowable insulating material on to the electrically conductive plate and allowing it to solidify.

7. A method according to claim 6, including the steps of placing the electrically conductive plate against the pre-moulded insert to form a first sub-assembly, placing the first sub-assembly into the jaw housing to form a second sub-assembly, and then placing the second sub-assembly into the second mould and injecting the second flowable insulating material.

8. A method according to claim 6, including the steps of placing the pre-moulded insert into the jaw housing to form a first sub-assembly, placing the electrically conductive plate on to the first sub-assembly to form a second sub-assembly, then placing the second sub-assembly into the second mould and injecting the second flowable insulating material.

9. A method according to claim 1, including the additional step of disposing an electrically conductive lead against the conductive plate before placing the jaw housing and the electrically conductive plate into the second mould.

10. A method according to claim 9, including the step of crimping the electrically conductive lead in position before placing the jaw housing and the electrically conductive plate into the second mould.

11. A method according to claim 10, wherein the second flowable insulating material assists in securing the lead in position in electrical connection with the conductive plate.

12. A method according to claim 1, wherein the through holes are disposed along the longitudinal axis of the conductive plate.

13. A method according to claim 1, wherein the elongate groove is substantially U-shaped.

14. A method according to claim 1, wherein the electrically conductive plate includes a longitudinally extending slot capable of receiving a translatable knife blade.

15. A method according to claim 1, wherein the electrically conductive plate includes a longitudinally extending slot capable of receiving a translatable knife blade, and wherein the one or more retention features are disposed adjacent the longitudinally extending slot.

16. A method according to claim 15, wherein the one or more retention features are disposed either side of the longitudinally extending slot.

17. A method for manufacturing a jaw member for an electrosurgical instrument, the method comprising the steps of:
   providing a jaw housing having a longitudinal jaw section;
   providing an electrically conductive plate with one or more retention features disposed adjacent to and either side of a longitudinally extending slot of the electrically conductive plate that is capable of receiving a translatable knife blade;
   placing the electrically conductive plate into a first mould;
   injecting a first flowable insulating material into the first mould, such that the first flowable insulating material flows into the one or more retention features to form one or more stop members that project a predetermined distance from the electrically conductive plate;
   allowing the first flowable insulating material to solidify;
   placing the jaw housing and the electrically conductive plate into a second mould;
   subsequently injecting a second flowable insulating material into the second mould to secure the electrically conductive plate to the jaw housing;
   allowing the second flowable insulating material to solidify; and
   removing the jaw housing, the electrically conductive plate, the solidified first insulating material, and the solidified second insulating material from the first mould and the second mould as a jaw member,
   wherein the one or more retention features comprise one or more indents in the longitudinally extending slot.

* * * * *